United States Patent
Yi et al.

(10) Patent No.: US 9,504,439 B2
(45) Date of Patent: Nov. 29, 2016

(54) X-RAY IMAGING APPARATUS AND CONTROL METHOD FOR THE SAME

(71) Applicant: SAMSUNG ELECTRONICS CO., LTD., Suwon-si (KR)

(72) Inventors: Jaemock Yi, Hwaseong-si (KR); Dong-Goo Kang, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 235 days.

(21) Appl. No.: 14/507,951

(22) Filed: Oct. 7, 2014

(65) Prior Publication Data

US 2015/0098550 A1  Apr. 9, 2015

(30) Foreign Application Priority Data

Oct. 7, 2013 (KR) .................. 10-2013-0119077

(51) Int. Cl.
*G01N 23/04* (2006.01)
*A61B 6/00* (2006.01)

(52) U.S. Cl.
CPC ............. *A61B 6/542* (2013.01); *A61B 6/4035* (2013.01); *A61B 6/4233* (2013.01); *A61B 6/469* (2013.01); *A61B 6/504* (2013.01); *A61B 6/5205* (2013.01); *A61B 6/405* (2013.01); *A61B 6/4441* (2013.01)

(58) Field of Classification Search
CPC ...... A61B 6/542; A61B 6/504; A61B 6/469; A61B 6/4233; A61B 6/4035; A61B 6/4441; A61B 6/5205; A61B 6/405; G01N 23/04
USPC ......................... 378/62, 98.2, 98.8
See application file for complete search history.

(56) References Cited

U.S. PATENT DOCUMENTS

| | | | |
|---|---|---|---|
| 7,876,962 B2 | 1/2011 | Staton | |
| 7,983,867 B2 | 7/2011 | Pavkovich et al. | |
| 2003/0058994 A1* | 3/2003 | Sembritzki | A61B 6/06 378/108 |
| 2005/0288882 A1 | 12/2005 | Pavkovich et al. | |
| 2009/0274354 A1 | 11/2009 | Ng et al. | |

FOREIGN PATENT DOCUMENTS

JP    2007-143982 A    6/2007

\* cited by examiner

*Primary Examiner* — Courtney Thomas
(74) *Attorney, Agent, or Firm* — Sughrue Mion, PLLC

(57) ABSTRACT

An X-ray imaging apparatus includes an X-ray source configured to radiate X-rays to a region of a subject, an X-ray detector configured to acquire a plurality of frame images related to the region of the subject by detecting the radiated X-rays, a filter configured to filter the X-rays radiated from the X-ray source, an image processor configured to set a region of interest within the region of the subject based on the plurality of frame images, and a controller configured to control the filter so that X-rays of a lower dose than a dose of X-rays made incident on the region of interest are made incident on a region of non-interest within the region of the subject, and control the X-ray detector so that a gain of the X-ray detector in the region of non-interest is greater than that in the region of interest.

20 Claims, 17 Drawing Sheets

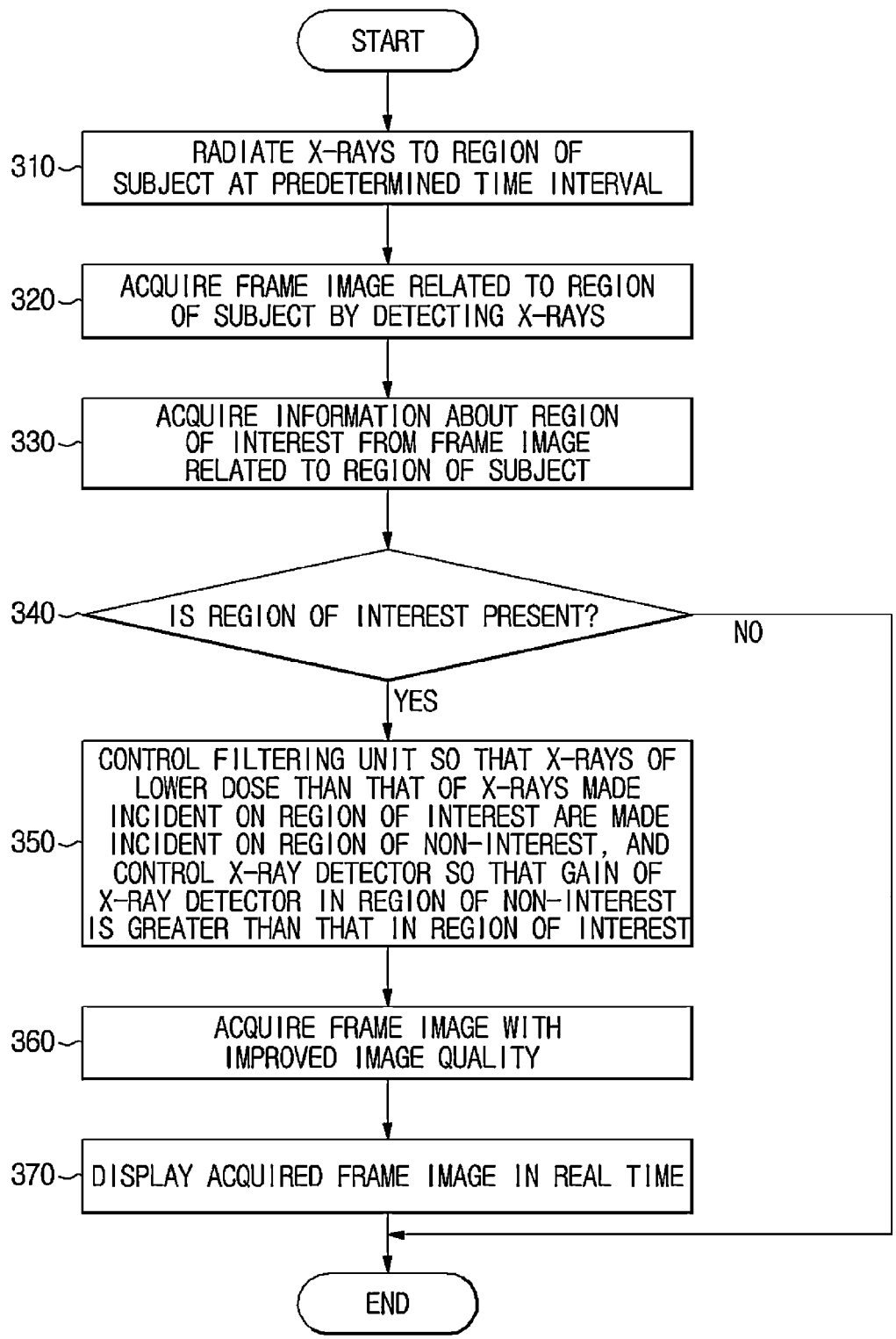

X-RAY IMAGING APPARATUS AND CONTROL METHOD FOR THE SAME

CROSS REFERENCE TO RELATED APPLICATION

This application claims the benefit of Korean Patent Application No. 10-2013-0119077, filed on Oct. 7, 2013 in the Korean Intellectual Property Office, the disclosure of which is incorporated herein by reference in its entirety.

BACKGROUND

1. Field

Exemplary embodiments relate to an X-ray imaging apparatus that radiates X-rays to a subject to visualize the inside of the subject and a control method for the same.

2. Description of the Related Art

An X-ray imaging apparatus is an apparatus that can radiate X-rays to a subject and acquire an internal image of the subject using the X-rays transmitted through the subject. Transmissivity of the X-rays is different according to characteristics of a material of which the subject is constituted, and therefore the internal structure of the subject can be visualized by detecting the intensity or strength of the X-rays transmitted through the subject.

Meanwhile, reducing the dose of X-rays of the subject in order to ensure the stability of the X-ray imaging apparatus is recognized as an important issue, and a variety of types of research and development for reducing the dose of X-rays are underway.

In commercially available technologies for reducing the dose of X-rays, a method of radiating X-rays only to a region of interest has been adopted, but such a method has a problem that it has to sacrifice a field of view (FOV) instead of reducing the dose of X-rays.

Thus, there is a need for research and development on technologies that can minimize a loss of FOV of an X-ray image while reducing the dose of X-rays.

SUMMARY

Therefore, it is an aspect of the exemplary embodiments to provide an X-ray imaging apparatus in which a region of interest and a region of non-interest may be divided and a gain of an X-ray detector as well as an incident dose of X-rays may differ for each region, and a control method for the same.

In addition, it is another aspect of the exemplary embodiments to provide an X-ray imaging apparatus in which movement of a region of interest is possible and a control method for the same.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an X-ray imaging apparatus including: an X-ray source configured to radiate X-rays to a region of a subject; an X-ray detector configured to acquire a plurality of frame images related to the region of the subject by detecting the radiated X-rays; a filter configured to filter the X-rays radiated from the X-ray source; an image processor configured to set a region of interest within the region of the subject based on the plurality of frame images; and a controller configured to control the filter so that X-rays of a lower dose than a dose of X-rays made incident on the region of interest are made incident on a region of non-interest within the region of the subject, and control the X-ray detector so that a gain of the X-ray detector in the region of non-interest is greater than a gain of the X-ray detector in the region of interest.

The control unit may be configured to control the gain of the X-ray detector based on a difference in the doses of the X-rays made incident on the region of non-interest and the region of interest.

Also, the controller may be configured to control the X-ray detector in such a manner that a gain difference between the gain of the X-ray detector in the region of non-interest and the gain of the X-ray detector in the region of interest is proportional to a difference between the dose of the X-rays made incident on the region of non-interest and the dose of the X-rays made incident on the region of interest.

The filter may include a filter for the region of interest that is made of a filter material for attenuating the X-rays, and a filter driver that may be configured to move the filter for the region of interest.

The image processor may be configured to acquire information about the region of interest and information about image characteristics based on the plurality of frame images, and to transmit the acquired information to the controller.

The information about the region of interest may be at least one of a position of the region of interest, a size of the region of interest, and a movement characteristic of the region of interest.

The controller may be configured to control the filter driver in such a manner that the filter driver moves the filter for the region of interest to a position corresponding to the region of non-interest based on the information about the region of interest.

The controller may be configured to determine a difference in the doses of the X-rays made incident on the region of non-interest and the region of interest based on the information about image characteristics.

The controller may be configured to control a kind or a thickness of the filter for the region of interest according to the determined difference in the doses of the X-rays.

Each pixel of the X-ray detector may include a variable amplifier or a plurality of amplifiers.

The controller may be configured to control the X-ray detector in such a manner that the amplifier of a pixel corresponding to the region of interest has a first gain, the amplifier of a pixel corresponding to the region of non-interest has a second gain, and the first gain is smaller than the second gain.

Each pixel of the X-ray detector may include a variable capacitance element.

The controller may be configured to control the X-ray detector in such a manner that the variable capacitance element of a pixel corresponding to the region of interest has a first capacitance, the variable capacitance element of a pixel corresponding to the region of non-interest has a second capacitance, and the first capacitance is greater than the second capacitance.

The image processor may be configured to perform setting of the region of interest in real time according to a frame rate.

In accordance with another aspect of an exemplary embodiment, there is provided a control method for an X-ray imaging apparatus, the control method including: radiating, by an X-ray source, X-rays to a region of a subject; acquiring, by an X-ray detector, a plurality of frame images related to the region of the subject by detecting the radiated X-rays; setting a region of interest within the region of the subject based on the plurality of frame images; filtering the X-rays radiated from the X-ray source so that X-rays of a lower dose than a dose of X-rays made incident on the region of interest are made incident on a region of non-interest within the region of the subject; and controlling the X-ray imaging apparatus in such a manner that a gain of the X-ray detector in the region of non-interest is greater than a gain in the region of interest.

The controlling may include controlling the gain of the X-ray detector based on a difference in the doses of the X-rays made incident on the region of non-interest and the region of interest.

The controlling may include controlling the X-ray imaging apparatus in such a manner that a gain difference of the X-ray detector in the region of non-interest and the region of interest is proportional to a difference in the doses of the X-rays made incident on the region of non-interest and the region of interest.

The control method for the X-ray imaging apparatus may further include acquiring information about the region of interest and information about image characteristics based on the plurality of frame images.

The filtering of the X-rays may include moving a filter for the region of interest that attenuates the radiated X-rays to a position corresponding to the region of non-interest based on the information about the region of interest.

The filtering of the X-rays may include determining a difference in the doses of the X-rays made incident on the region of non-interest and the region of interest based on the information about image characteristics.

The filtering of the X-rays may include controlling a kind or a thickness of the filter for region of interest according to the determined difference in the doses of the X-rays.

The controlling may include controlling the X-ray imaging apparatus in such a manner that, when each pixel of the X-ray detector includes a variable amplifier or a plurality of amplifiers, the amplifier of a pixel corresponding to the region of interest has a first gain, and the amplifier of a pixel corresponding to the region of non-interest has a second gain, setting the first gain to be smaller than the second gain.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 17 is a flowchart illustrating a control method for an X-ray imaging apparatus in accordance with an exemplary embodiment.

DETAILED DESCRIPTION

Hereinafter, an X-ray imaging apparatus in accordance with an exemplary embodiment and a control method for the X-ray imaging apparatus will be described in detail with reference to the accompanying drawings.

The structure or radiography method of the X-ray imaging apparatus may be changed depending on the purpose of radiography, a field of view (FOV), or the kind of an X-ray image, such as an X-ray imaging apparatus using fluoroscopy, an X-ray imaging apparatus using angiography, and the like.

Figure 1:
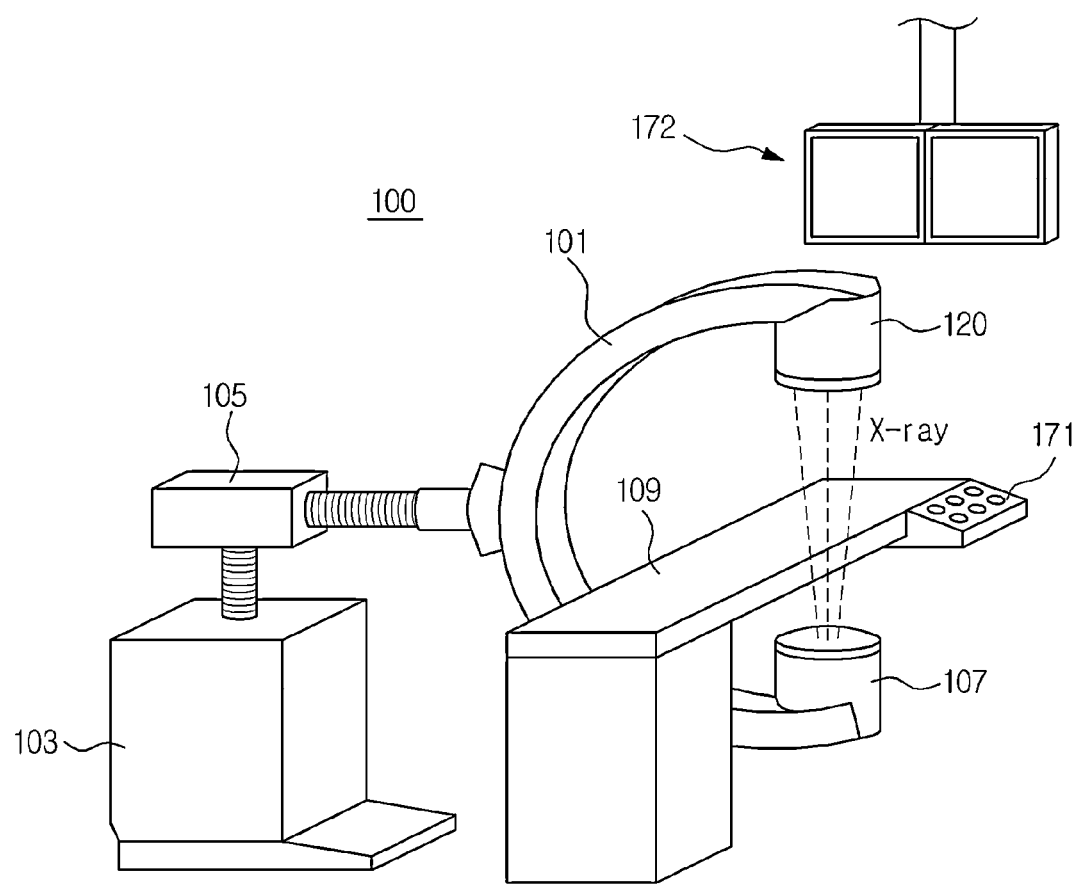
FIG. 1 is a diagram illustrating the appearance of an X-ray imaging apparatus.

FIG. 1 is a diagram illustrating the appearance of an X-ray imaging apparatus.

The X-ray imaging apparatus 100 may include an X-ray source assembly 107, an X-ray detector 120, a table 109, a main body 103, an input unit 171, and a display unit 172, and may have a C-arm structure as shown in FIG. 1.

The X-ray source assembly 107 may include an X-ray source (see 110 of FIG. 2) that generates X-rays and radiates the generated X-rays to a subject and a filtering unit (see 140 of FIG. 2) that filters the X-rays radiated from the X-ray source 110, and may be mounted on one end of a C-arm 101. Here, the subject is a target of X-ray radiography or a subject to be diagnosed, and the subject is not limited as long as the internal structure of the subject can be visualized by the X-ray imaging apparatus 100.

The X-ray detector 120 may be mounted on the other end of the C-arm 101, and may be positioned on an opposite side of the X-ray source assembly 107 while interposing the table 109 therebetween. Thus, when the X-ray source 110 radiates X-rays to a subject positioned on the table 109, the X-ray detector 120 may detect the X-rays transmitted through the subject. In addition, the X-ray detector 120 may convert the detected X-rays into electrical signals.

The C-arm 101 may be rotatable in an orbital direction, and connected to the main body 103 through a connection axis 105.

Figure 2:
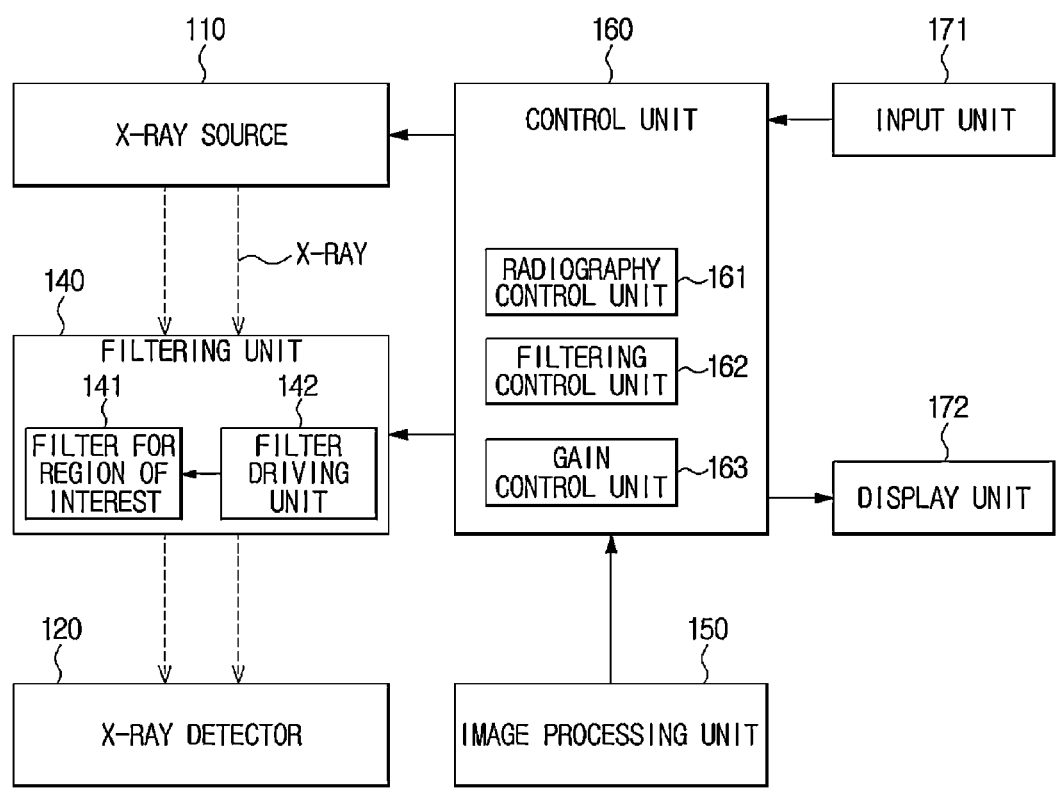
FIG. 2 is a control block diagram illustrating an X-ray imaging apparatus in accordance with an exemplary embodiment.

The main body 103 may accommodate main components of the X-ray imaging apparatus 100, for example, a control unit (see 160 of FIG. 2). The control unit 160 may generate a variety of control signals for operations of the X-ray imaging apparatus 100 such as controlling a dose of the X-rays radiated from the X-ray source 110, or controlling a gain of the X-ray detector 120, and this will be described in detail later.

The input unit 171 may be provided on a side surface of the table 109 and receive commands related to operations of the X-ray imaging apparatus from a user, and the commands received from the input unit 171 may be transmitted to the main body 103 through wired or wireless communication. Here, the user may be a person who performs diagnosis of a subject using the X-ray imaging apparatus 100, that is, a medical staff including a doctor, a radiologist, a nurse, and the like, but is not limited thereto. The user is not limited as long as the user can use the X-ray imaging apparatus 100.

The input unit 171 may include at least one of a switch, a keyboard, a trackball, and a touch screen, but is not limited thereto.

The display unit 172 may display an image obtained in an X-ray diagnosis process, and may be mounted on a ceiling through a holder so that a user can see the display image.

The display unit 172 may be implemented as a cathode ray tube (CRT), a liquid crystal display (LCD), a light emitting diode (LED), and the like, but is not limited thereto.

FIG. 2 is a control block diagram illustrating an X-ray imaging apparatus in accordance with an exemplary embodiment.

Referring to FIG. 2, the X-ray imaging apparatus 100 may generate an X-ray video related to a region of a subject by the X-ray source 110, the filtering unit 140 (e.g., filter), the X-ray detector 120, an image processing unit 150 (e.g., image processor), the control unit 160 (e.g., controller), the input unit 171 (e.g., inputter), and the display unit 172 (e.g., display).

Here, the region of the subject is a predetermined region including a subject, and refers to a region visualized as an X-ray image. Thus, the region of the subject may correspond to a field of view (FOV) of the X-ray imaging apparatus 100 or include a radiography region of the X-ray imaging apparatus 100. In addition, the region of the subject includes at least one of a region of interest and a region of non-interest. A region that is not the region of interest among the region of the subject is the region of non-interest, and the region of interest and the region of non-interest will be described in detail later.

Figure 3:
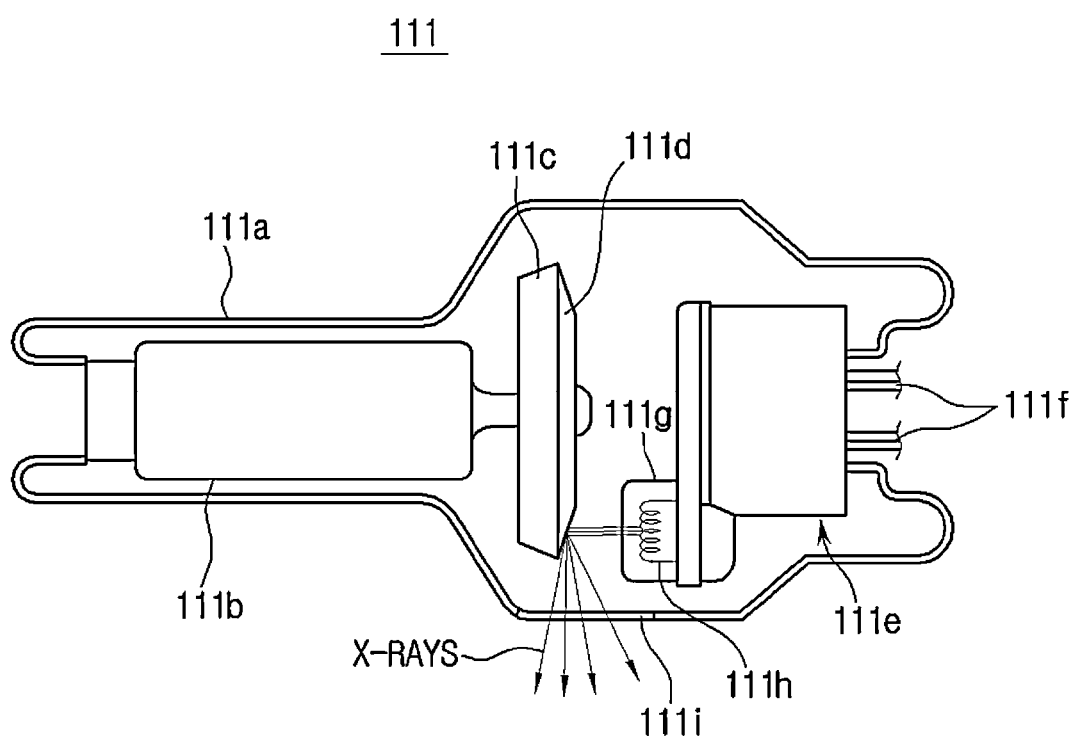
FIG. 3 is a cross-sectional diagram illustrating an internal structure of an X-ray tube.

The X-ray source 110 may generate X-rays to radiate the generated X-rays to a subject, and include an X-ray tube 111 for generating X-rays as shown in FIG. 3. FIG. 3 is a cross-sectional diagram illustrating an internal structure of an X-ray tube.

The X-ray tube 111 may be implemented as a diode vacuum tube including an anode 111c and a cathode 111e, and the tubular body may be a glass tube 111a made of a rigid silicate glass or the like.

The cathode 111e includes a focusing electrode 111g that focuses filaments 111h and electrons, and the focusing electrode 111g may be referred to as a focusing cup. Thermoelectrons are generated in such a manner that the inside of the glass tube 111a is in a high vacuum state of approximately 10 mmHg and the filaments 111h of the cathode are heated to a high temperature. As an example of the filaments 111h, tungsten filaments may be used, and the filaments 111h may be heated by applying a current to an electric lead wire 111f connected to the filaments 111h. However, the disclosed exemplary embodiment is not limited to adopting the filaments 111h in the cathode 111e, and a carbon nanotube that can be driven by a high-speed pulse may be used as the cathode 111e.

The anode 111c may be mainly made of copper, and a target material 111d may be coated or disposed on a side of the anode 111c that faces the cathode 111e. As the target material, high-resistance materials such as Cr, Fe, Co, Ni, W, Mo, and the like may be used. A focal spot size is reduced along with an increase in the melting point of the target material.

When a high voltage is applied between the cathode 111e and the anode 111c, the thermoelectrons are accelerated and collide with the target material 111d of the anode to generate X-rays. The generated X-rays are radiated to the outside through a window 111i, and a beryllium (Be) thin film may be used as a material of the window.

The target material 111d may be rotated by a rotor 111b, and when the target material 111d is rotated, a heat accumulation rate may be increased 10 times or more per unit area compared to a case in which the target material 111d is fixed, and the focal spot size may be reduced.

The voltage applied between the cathode 111e and the anode 111c of the X-ray tube 111 is referred to as a tube voltage, and the magnitude of the tube voltage may be represented as a crest value kvp. When the tube voltage is increased, the speed of the thermoelectrons is increased and the thermoelectrons collide with the target material to generate X-rays, and therefore energy (energy of photons) of the generated X-rays is increased. A current flowing in the X-ray tube 111 may be referred to as a tube current, and represented as a mean value mA. When the tube current is increased, the dose of the X-rays (the number of photons of X-rays) is increased. That is, the energy of the X-rays may be controlled by the tube voltage, and the dose of the X-rays may be controlled by the tube current and an X-ray exposure time.

Meanwhile, in order to generate an X-ray video, the X-ray tube 111 should continuously generate X-rays, and for this, a continuous exposure method and a pulse exposure method may be applied. Specifically, in a case of applying the continuous exposure method, X-rays are continuously generated by continuously supplying a low tube current to the X-ray tube 111, and in a case of applying the pulse exposure method, X-rays are generated according to a series of short pulses. Thus, when applying the pulse exposure method, the dose of the X-rays and motion blurring may be reduced. Hereinafter, for convenience of description, the pulse exposure method will be described in detail.

The X-ray source 110 may radiate X-rays to a subject at a predetermined time interval multiple times, using the above-described X-ray tube 111. Here, the predetermined time interval may be determined according to a pulse rate or a frame rate, and the pulse rate may be determined according to the frame rate. For example, the frame rate may be set as 30 frames per second (30 fps), 15 frames per second (15 fps), 7.5 frames per second (7.5 fps), or the like.

The filtering unit 140 may include a filter 141 for a region of interest and a filter driving unit 143 (e.g., filter driver).

The filter 141 for a region of interest is made of a material for absorbing X-rays and may filter X-rays radiated from the X-ray source 110 so that X-rays of a lower dose than that of X-rays made incident on the region of interest are made incident on the region of non-interest. This feature is for reducing the dose of X-rays. X-rays of a larger dose than that of X-rays applied to the region of non-interest are applied to the region of interest having a large amount of useful information about the inside of the subject through X-ray filtering, and X-rays of a smaller dose than that of X-rays applied to the region of interest are applied to the region of non-interest having a small amount of information. In this instance, the X-rays are made incident even on the region of non-interest, and therefore a loss of the FOV may not occur.

The filter driving unit 143 is provided for moving the filter 141 for a region of interest, and may include a motor that generates power and a mechanical structure that transmits the generated power to the filter 141 for a region of interest such as a gear or the like.

The more specific structure and operation of the filtering unit 140 will be described later.

The X-ray detector 120 detects X-rays transmitted through the subject, and converts the detected X-rays into electrical signals to acquire a plurality of frame images about the region of the subject. Here, the frame image refers to each of a plurality of X-ray images acquired according to a frame rate of the X-ray imaging apparatus 100.

The X-ray detector 120 may be classified in accordance with a material of which the X-ray detector 120 is constituted, a method of converting the detected X-rays into electrical signals, or a method of acquiring electrical signals.

First, the X-ray detector 120 is classified as being constituted of a single element or constituted of a mixed element in accordance with the material of which it is constituted.

A case in which the X-ray detector 120 is constituted of the single element corresponds to a case in which a portion that detects X-rays to generate electrical signals and a portion that reads and processes electrical signals are constituted of a semiconductor composed of a single material or manufactured in a single process, and for example, corresponds to a case in which a single light-receiving element such as a charge coupled device (CCD) or a complementary metal oxide semiconductor (CMOS) is used.

A case in which the X-ray detector 120 is constituted of the mixed element corresponds to a case in which the portion that detects X-rays to generate electrical signals and the portion that reads and processes electrical signals are constituted of different materials or manufactured in different processes. For example, there are cases in which the X-rays are detected using a light-receiving element such as a photodiode, a CCD, or CdZnTe and the electrical signals are read and processed using a CMOS read out integrated circuit (ROIC), cases in which the X-rays are detected using a strip detector and the electrical signals are read and processed using the CMOS ROIC, cases in which an a-Si or a-Se flat panel system is used, and the like.

In addition, the method in which the X-ray detector 120 converts the X-rays into electrical signals is classified as a direct conversion method or an indirect conversion method.

In the direct conversion method, when X-rays are radiated, electron-hole pairs are temporarily generated inside a light-receiving element, and the electrons move to the anode and the holes move to the cathode due to the electric field applied to both ends of the light-receiving element. Here, the X-ray detector 120 converts such movement into electrical signals. In the direct conversion method, a-Se, CdZnTe, $HgI_2$, $PbI_2$, or the like may be used as a material of the light-receiving element.

In the indirect conversion method, when X-rays radiated from the X-ray source 110 react with a scintillator to emit photons having wavelengths of the visible light region, the light-receiving element detects the emitted photons and converts the detected photons into electrical signals. In the indirect conversion method, a-Si or the like may be used as the light-receiving element, and a thin-film GADOX scintillator, a CSI (T1) having a micro columnar or needle structure, or the like may be used as the scintillator.

In addition, the method in which the X-ray detector 120 acquires electrical signals is classified as a charge integration mode of storing charges for a certain time and then acquiring signals from the stored charges, or a photon counting mode of performing counting every time when signals are generated by a single X-ray photon.

Any method among the above-described methods may be applied to the X-ray detector 120, but hereinafter, for convenience of description, a case in which the direct conversion method that directly acquires electrical signals from X-rays, a hybrid method in which a sensor chip for detecting X-rays and a read-out circuit chip are coupled, and the photon counting mode are applied will be described.

The X-ray detector 120 may have a two-dimensional (2D) array structure including a plurality of pixels, and when converting the detected X-rays into electrical signals for each pixel, a single X-ray image related to the region of the subject may be acquired.

In addition, the X-ray detector 120 controls a gain of the X-ray detector in the region of non-interest to be higher than that in the region of interest, and therefore image quality of the region of non-interest may be improved.

The structure and control of the gain of the X-ray detector 120 will be described in detail later.

The image processing unit 150 may analyze the frame images acquired by the X-ray detector 120 to acquire information about image characteristics, specifically, information such as noise or contrast that occurs in the frame image. The acquired information about image characteristics may be transmitted to the control unit 160 to be used in control of the X-ray source 110 or the filtering unit 140, and this will be described later.

In addition, the image processing unit 150 may acquire information about the region of interest by analyzing the frame images, and an operation in which the image processing unit 150 acquires the information about the region of interest will be described in detail.

First, the image processing unit 150 detects an object of interest from the frame image about the region of the subject.

Here, the object of interest is an object that should be continuously observed closely by a user during X-ray radiography, and may be an instrument used for the subject or an operation part. For example, in a case in which the X-ray imaging apparatus 100 uses angiography, when an instrument such as a guide wire, a catheter, a needle, a balloon, or a stent is inserted into the blood vessel, close observation is required, and therefore the image processing unit 150 may set the instrument as the object of interest. In addition, the image processing unit 150 may set an operation part such as stenosis, aneurysm, a cancerous region, or the like as the object of interest.

In order to detect the object of interest, the image processing unit 150 may previously store characteristics of the object of interest, and detect an object corresponding to the previously stored characteristics from the frame image about the region of the subject. For example, among the characteristics of the object of interest such as shape, X-ray absorption characteristics, movement characteristics, and the like, characteristics that can be detected from the X-ray image may be stored in advance.

Here, the movement characteristics of the object of interest may include information such as a size of the movement of the object of interest, a moving direction, and the like, and the movement of the object of interest may include transfer of the object of interest. The size of the movement may include speed, but the movement of the object of interest may not have a constant pattern. Thus, the size of the movement may include a variety of information indicating the degree of movement as well as the speed.

When the object of interest is detected, the image processing unit 150 sets a predetermined region including the detected object of interest as the region of interest. In this instance, the position and size of the region of interest may be determined considering the position, the size, or movement characteristics of the object of interest, and uncertainty that the movement characteristics of the object of interest have may be also considered. For example, when uncertainty is large because the movement of the object of interest is large or the movement characteristics of the object of interest are difficult to predict, the size of the region of interest may be set to be large.

Figure 4:
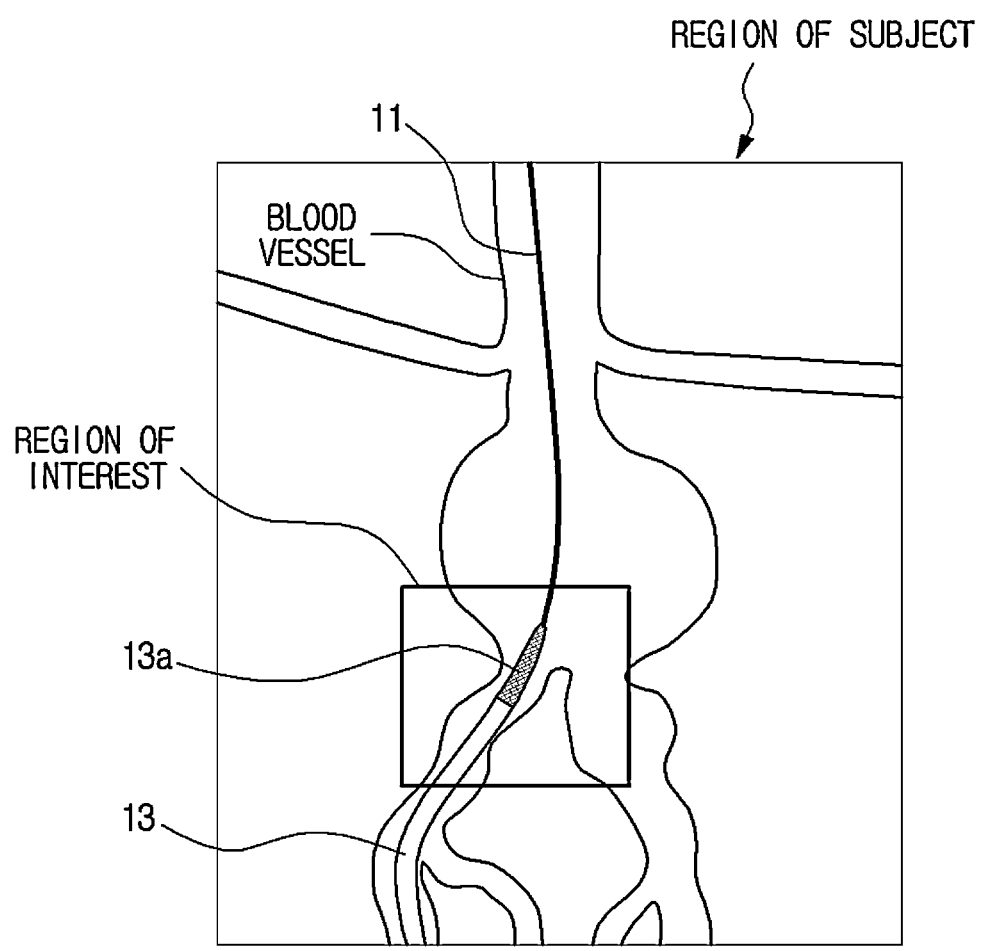
FIG. 4 is a diagram illustrating a region of interest in vascular stent implantation.

FIG. 4 is a diagram illustrating a region of interest in vascular stent implantation.

A stent 13a is injected into the blood vessel in order to prevent occlusion of the blood vessel, and has a mesh shape. The stent 13a is mounted on an end of a long tube-shaped stent instrument 13 to be injected into the blood vessel while being folded, and is unfolded with a mesh shape in a required position.

Referring to FIG. 4, in order to insert the stent instrument 13 into the blood vessel of the region of the subject, a guide wire 11 is first inserted, and the stent instrument 13 is inserted into the blood vessel along the guide wire 11.

The guide wire 11 or a tip of the guide wire 11 may be the object of interest while the guide wire 11 is inserted. While being inserted, the stent instrument 13, particularly, the stent 13a of the end portion of the stent instrument 13, may be the object of interest, or a predetermined region including the stent 13a may be the region of interest. Although not shown, while a catheter is inserted in order to inject a contrast medium into the blood vessel, the catheter or an end portion of the catheter may be the object of interest.

Meanwhile, the image processing unit 150 may use information input from the outside when detecting the object of interest. Specifically, when a kind of the instrument, a kind of operation, information about an operation part, and information about whether a contrast medium is injected are input, the object of interest may be detected from the frame image based on the input information.

For example, when information is input indicating that an operation to be performed is aortic stent implantation and an instrument to be inserted is a stent instrument, the image processing unit 150 detects a stent within the aorta from the frame image about a region of a subject using information about characteristics of the stent stored in advance.

In addition, the image processing unit 150 may set the region of interest while tracking the detected object of interest. In this instance, detecting and tracking of the object of interest, and setting of the region of interest may be performed in real time according to a frame rate of the frame images input to the image processing unit 150.

Through the setting of the region of interest, the image processing unit 150 may acquire information about the region of interest. Here, the information about the region of interest includes a position and a size of the region of interest, movement characteristics, and the like, and the movement characteristics of the region of interest are defined by movement characteristics of the object of interest. The acquired information about the region of interest may be transmitted to the control unit 160 to be used in controlling the X-ray source 110 or the filtering unit 140. This will be described in detail later.

Meanwhile, the image processing unit 150 may perform image correction or image enhancement for improving overall image quality of the frame image.

For example, the image processing unit 150 may perform correction of the frame image using a spatial filter, a temporal filter, a spatio-temporal filter, and a denoising algorithm such as super-resolution reconstruction. In addition, the image processing unit 150 may perform enhancement of the frame image using a detail enhancement algorithm such as a contrast enhancement algorithm based on histogram or wavelet, an edge enhancement filter, and the like.

The control unit 160 may include a radiography control unit 161, a filtering control unit 162, and a gain control unit 163.

The radiography control unit 161 controls the X-ray source 110, and more specifically, controls various radiography parameters applied to X-ray radiography. The radiography parameter may be referred to as an exposure parameter, and automatically controlling the radiography parameter in the X-ray imaging apparatus 100 is referred to as auto exposure control.

The radiography parameter may be at least one selected from a group consisting of a tube voltage, a tube current, an exposure time, a kind of a filter, an FOV, a frame rate, a pulse rate, a dose per frame, and the like.

The radiography parameter may be determined based on the frame image about the region of the subject or based on advance information input before starting radiography, but a case of the former will be hereinafter described in detail.

When the radiography control unit 161 determines the radiography parameter such as a frame rate, a tube current, a dose per frame, and the like and separately or simultaneously controls the determined radiography parameter, the information about the region of interest acquired from the image processing unit 150 may be used. For example, the radiography control unit 161 may maximally acquire information about the movement of the object of interest by increasing the frame rate when the size of the movement of the object of interest is large, and reduce the exposure of the subject by reducing the frame rate when the size of the movement of the object of interest is small.

In addition, when the radiography control unit 161 controls the radiography parameter, the information about image characteristics acquired from the image processing unit 150 may be used. For example, when a noise level of the region of interest is higher than a predetermined reference value, the radiography control unit 161 may reduce the noise level by increasing the dose per frame so that the region of interest can be seen more clearly, and when the noise level of the region of interest is lower than the predetermined reference value, the radiography control unit 161 may reduce the exposure of the subject by reducing the dose per frame.

The filtering control unit 162 controls the filtering unit 140 based on the information about the region of interest acquired from the image processing unit 150. In order to describe operations of the filtering control unit 162, the configuration of the filtering unit 140 will be described in detail with reference to FIGS. 5 and 6.

Figure 5:
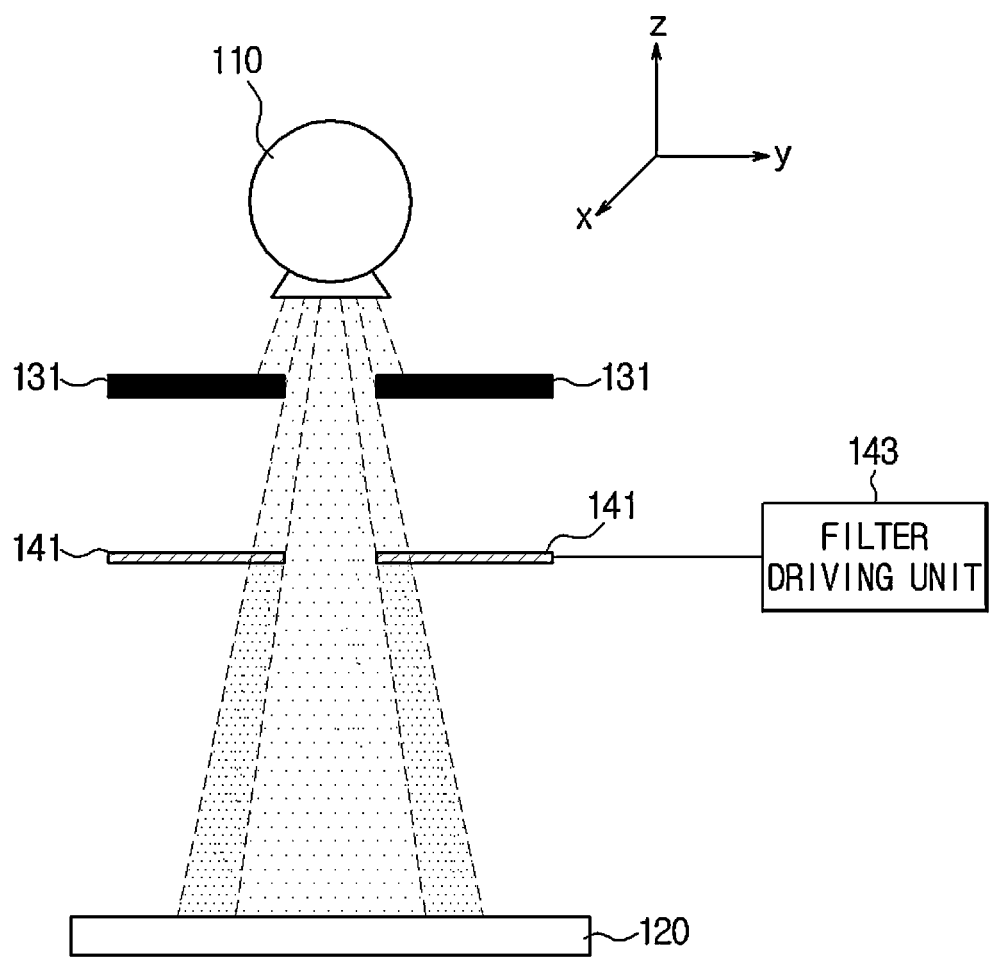
FIG. 5 is a side cross-sectional diagram illustrating a filtering unit in which a filter for a region of interest is provided.
Figure 6:
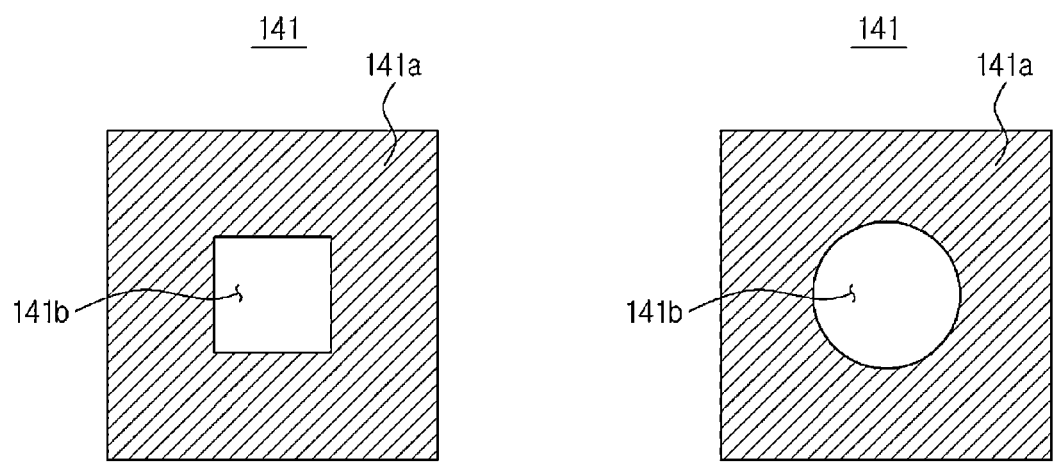
FIG. 6 is a plan diagram illustrating an example of a filter for a region of interest.

FIG. 5 is a side cross-sectional diagram illustrating a filtering unit in which a filter for a region of interest is provided, and FIG. 6 is a plan diagram illustrating an example of a filter for region of interest.

Referring to FIG. 5, as described above, the filtering unit 140 includes the filter 141 for a region of interest and the filter driving unit 143 for moving the filter 141 for a region of interest.

The filter 141 for a region of interest may be moved on an x-y plane or z-axis by the filter driving unit 143. The movement on the x-y plane is used for associating the filter 141 for a region of interest with a position of the region of non-interest, and the movement on the z-axis is used for associating the filter 141 for a region of interest with a size of the region of interest.

In front of the X-ray source 110, that is, in a direction of X-ray radiation, a collimator 131 may be disposed. The collimator 131 may be made of a material that absorbs or blocks X-rays such as lead or tungsten, and adjusts a range of FOV and reduces scattering of X-rays.

The filter 141 for a region of interest may be positioned between the collimator 131 and the X-ray detector 120 to filter X-rays radiated from the X-ray source 110. The filter 141 for a region of interest may be made of a material that attenuates X-rays, and X-rays are attenuated while passing through the filter 141 for a region of interest, and thereby the dose of the X-rays may be reduced. Thus, when the filter 141 for a region of interest is positioned in a position corresponding to the region of non-interest among the region of the subject, X-rays of a smaller dose than that of X-rays made incident on the region of interest may be made incident on the region of non-interest.

The region of interest is generally surrounded by the region of non-interest, and therefore the filter 141 for a region of interest may have a ring shape whose center is empty, that is, a ring shape with an opening 141b formed at the center thereof, as shown in FIG. 6.

As shown on the left side of FIG. 6, the opening 141b may be a polygon or as shown on the right side of FIG. 6, the opening 141b may be a circle, but the shape of the filter 141 for a region of interest is not limited thereto. For example, the filter 141 for a region of interest may have a variety of shapes according to characteristics of the region of interest or a relationship between the region of interest and the region of non-interest.

Hereinafter, operations of the filtering control unit 162 will be described based on the above-described configuration of the filtering unit 140.

The filtering control unit 162 may generate control signals for moving the filter 141 for a region of interest based on information about the region of interest, and transmit the generated control signals to the filter driving unit 143, thereby moving the filter 141 for a region of interest to a position corresponding to the region of non-interest.

Specifically, the filtering control unit 162 may control movement on the x-y plane of the filter 141 for a region of interest so that the opening 141b of the filter 141 for a region of interest is positioned in the position corresponding to the region of interest, and control movement on the z-axis of the filter 141 for a region of interest so that the opening 141b of the filter 141 for a region of interest corresponds to the size of the region of interest.

The filtering control unit 162 may control a kind or a thickness of the filter 141 for a region of interest as well as the position of the filter 141 for a region of interest. In this instance, the filtering control unit 162 may determine a difference in doses of X-rays to be made incident on the region of non-interest and the region of interest based on information about image characteristics such as noise, motion, contrast, and the like, and variably control the kind or the thickness of the filter 141 for a region of interest according to the determined difference in the doses. Hereinafter, operations of the filtering control unit 162 that control the kind or the thickness of the filter 141 for region of interest will be described with reference to FIG. 7.

Figure 7:
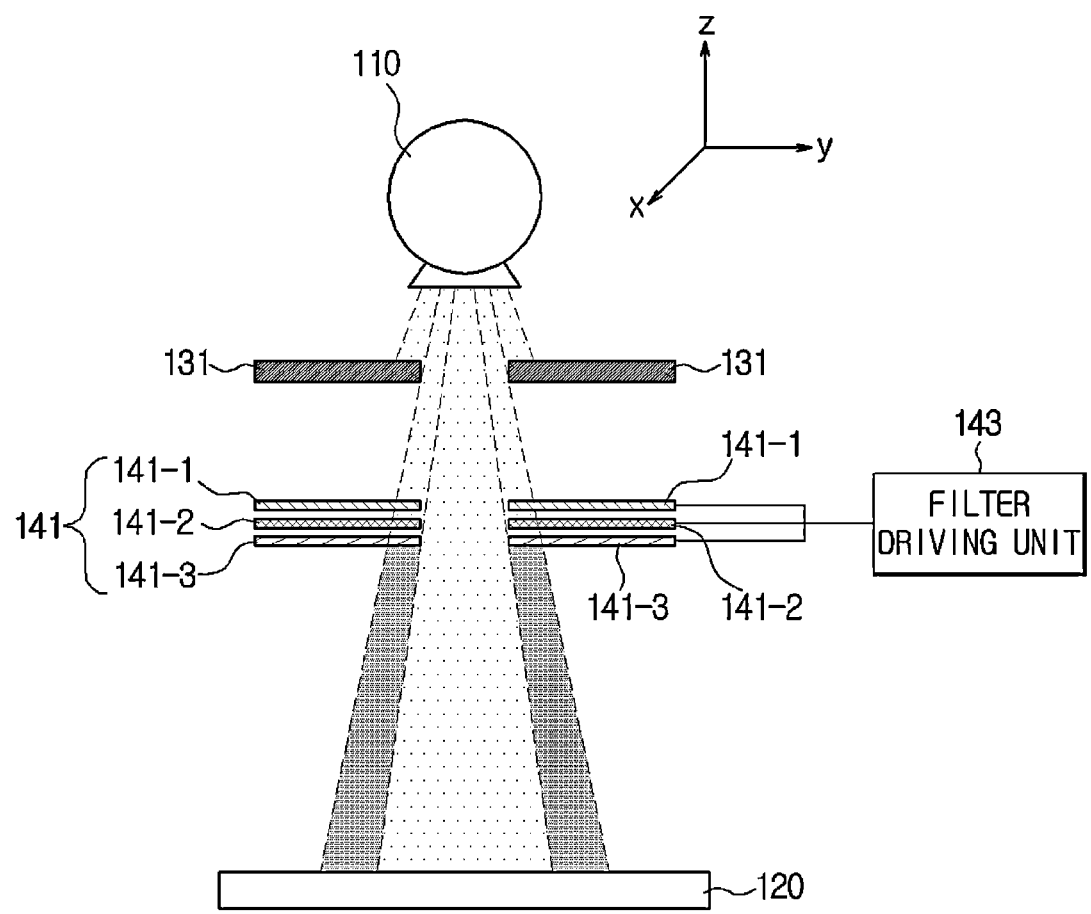
FIG. 7 is a side cross-sectional diagram illustrating a filtering unit in which a plurality of filters for a region of interest are provided.

FIG. 7 is a side cross-sectional diagram illustrating a filtering unit in which a plurality of filters for a region of interest is provided.

Referring to FIG. 7, the filter 141 for a region of interest may be constituted of a plurality of filter layers that can be independently moved on the x-y plane or the z-axis, and the respective filter layers may be a first filter 141-1 for a region of interest, a second filter 141-2 for a region of interest, and a third filter 141-3 for a region of interest.

The first filter 141-1 for a region of interest, the second filter 141-2 for a region of interest, and the third filter 141-3 for a region of interest may have the same kind of the filtration material and a different thickness thereof, a different kind of the filtration material and a different thickness thereof, a different kind of the filtration material and the same thickness thereof, or the same kind of the filtration material and the same thickness thereof.

The filtering control unit 162 may determine the difference in the doses of X-rays to be made incident on the region of interest and the region of non-interest based on the information about image characteristics, and determine a combination of the first filter 141-1 for a region of interest, the second filter 141-2 for a region of interest, and the third filter 141-3 for a region of interest so that X-rays are made incident according to the determined difference in the doses.

For example, when it is determined that the second filter 141-2 for a region of interest and the third filter 141-3 for a region of interest are required, the filtering control unit 162 may enable the second filter 141-2 for a region of interest and the third filter 141-3 for a region of interest to be positioned in a filtering position, and exclude the first filter 141-1 for a region of interest from the filtering position. Here, the filtering position refers to a position in which X-rays radiated from the X-ray source 110 or X-rays passing through the collimator 131 can be filtered.

The filtering control unit 162 may control the position of the filter 141 for a region of interest by moving the filter 141 for a region of interest on the z-axis or on the x-y plane. When the filter 141 for a region of interest is moved on the z-axis, a width of X-rays passing through the opening 141b of the filter 141 for a region of interest is reduced as the filter 141 for a region of interest is closer to the X-ray source 110 or the collimator 131, and therefore the X-rays may be deviated from the filtering position.

Figure 8:
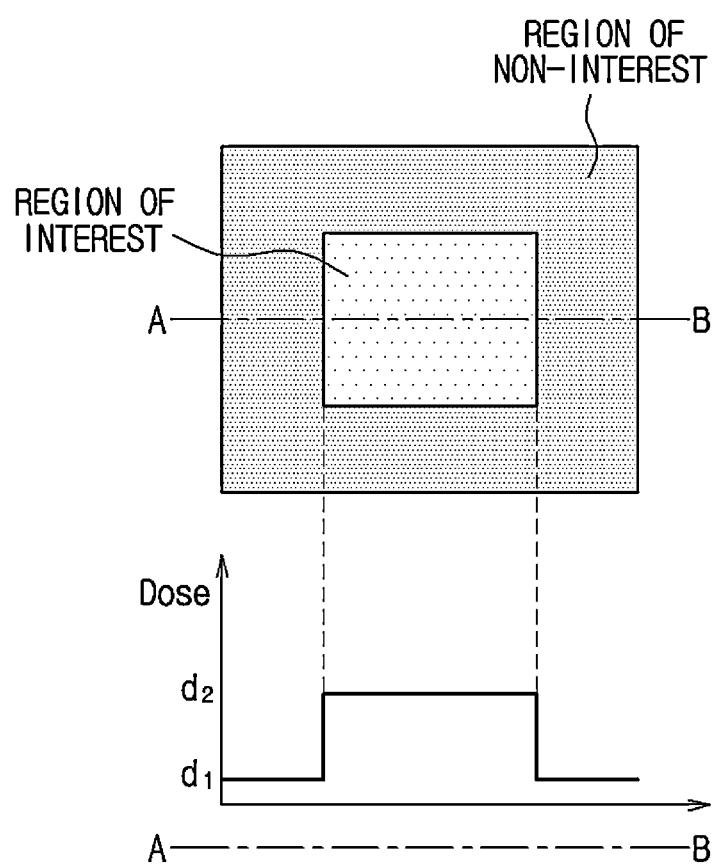
FIGS. 8 and 9 are schematic diagrams illustrating the dose of X-rays made incident on a region of interest and a region of non-interest.
Figure 9:
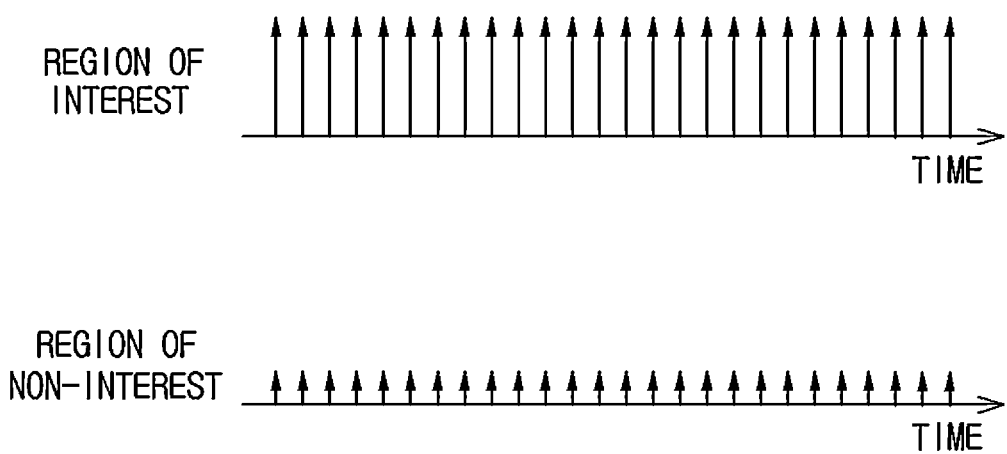

FIGS. 8 and 9 are schematic diagrams illustrating the dose of X-rays made incident on a region of interest and a region of non-interest.

FIG. 8 shows a dose of X-rays made incident on an arbitrary straight line AB that crosses the region of interest and the region of non-interest. When the filtering control unit 162 moves the filter 141 for a region of interest to a position corresponding to the region of non-interest, X-rays of a smaller dose than that of X-rays made incident on the region of interest may be made incident on the region of non-interest ($d1<d2$), as shown in FIG. 8. Despite a small dose, the X-rays are made incident even on the region of non-interest, and therefore information about the entire radiography region may be acquired.

As described above, the X-ray imaging apparatus 100 may acquire videos by continuously performing X-ray radiography, and a difference in the doses of the X-rays which are made incident on the region of interest and the region of non-interest may be maintained as shown in FIG. 9 as long as there is the region of interest in the region of the subject.

Figure 10:
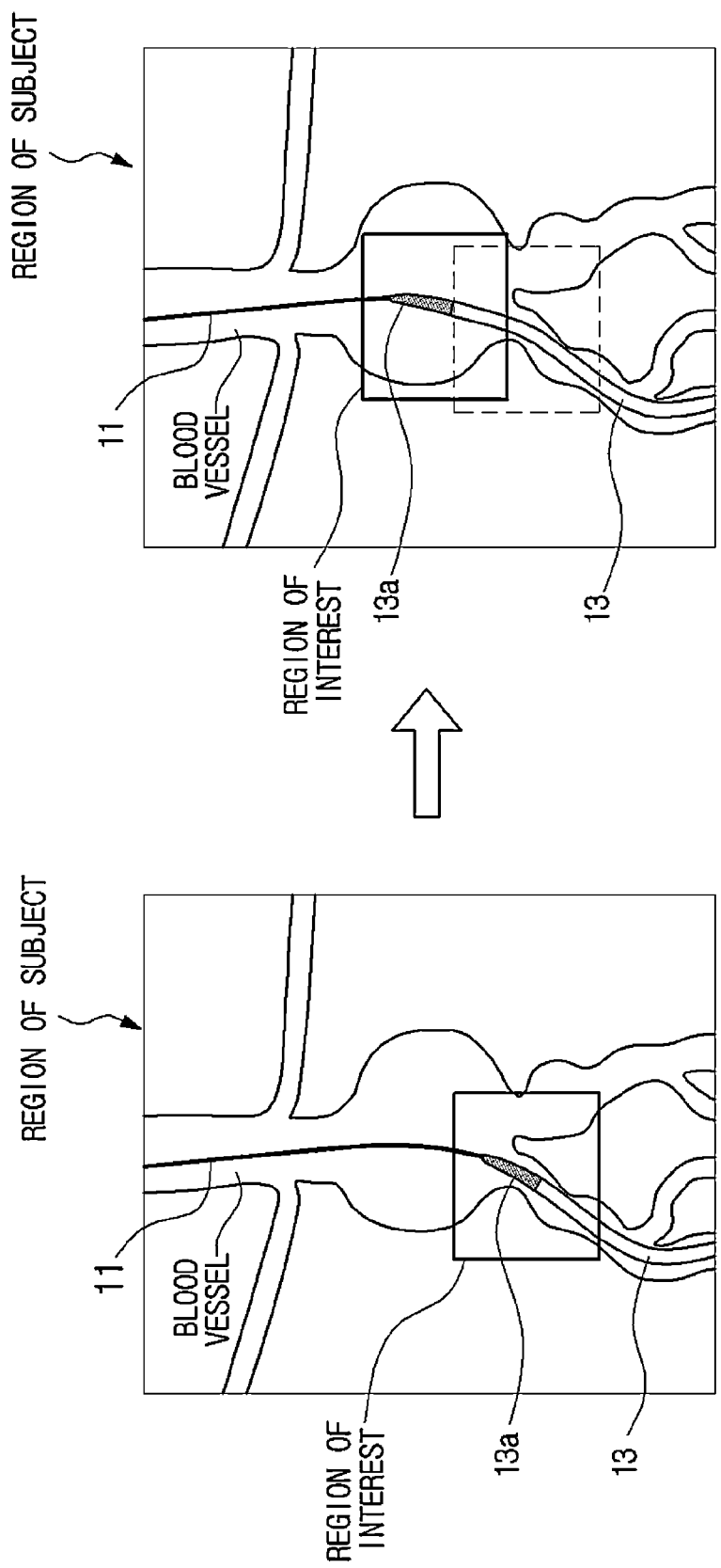
FIG. 10 is a diagram illustrating movement of a region of interest according to movement of an object of interest.
Figure 11:
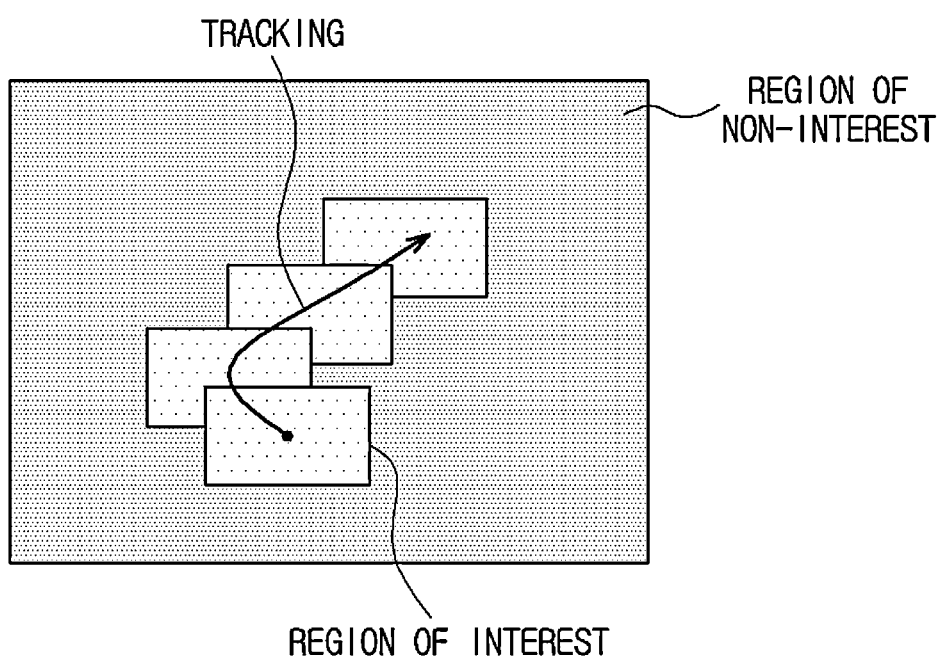
FIG. 11 is a schematic diagram illustrating an operation of tracking a moving region of interest.

FIG. 10 is a diagram illustrating movement of a region of interest according to movement of an object of interest, and FIG. 11 is a schematic diagram illustrating an operation of tracking a moving region of interest.

An X-ray video may represent movement that exists in the region of the subject, and when a subject of the movement is the object of interest, the region of interest may be moved by movement of the object of interest. For example, when stent implantation that inserts the stent instrument 13 into the blood vessel is carried out as shown in FIG. 10, the stent 13a that is the object of interest may be moved to a target position within the blood vessel, and the region of interest may be also moved depending on the movement of the stent 13a.

As described above, the image processing unit 150 may perform detecting and tracking of the object of interest and setting of the region of interest in real time. Thus, when the object of interest is moved, the image processing unit 150 tracks the movement of the object of interest in real time to set the region of interest as shown in FIG. 11. In other words, the image processing unit 150 moves the region of interest in real time. The filtering control unit 162 may move the filter 141 for a region of interest on the x-y plane, so that the filter 141 for a region of interest is synchronized with the movement of the region of interest to be moved together.

Meanwhile, in an example of FIG. 11, the region of interest is also moved along the movement of the object of interest, but the size of the region of interest may be changed according to the movement of the object of interest.

For example, when the size of the movement of the object of interest is not large, that is, when the size of the movement of the object of interest is a predetermined reference value or less, the image processing unit 150 may increase the size of the region of interest while fixing the position of the region of interest so that the region of interest includes the object of interest. Thus, an increase rate of the size of the region of interest may differ according to the size of the movement of the object of interest. In this case, the filtering control unit 162 may move the filter 141 for a region of interest only on the z-axis without moving the filter 141 for a region of interest on the x-y plane, and therefore a position of the filter 141 for a region of interest on the z-axis may be synchronized with the change in the size of the region of interest.

The gain control unit 163 controls the X-ray detector 120, and more specifically, controls a gain of the X-ray detector 120 in the region of interest and the region of non-interest.

When X-rays of a smaller dose than that of X-rays made incident on the region of interest are made incident on the region of non-interest, a signal to noise ratio (SNR) in the region of non-interest appears lower than that in the region of interest, and an image quality difference between the region of interest and the region of non-interest within the image of the subject may be generated. That is, the image quality of the region of non-interest having a lower SNR is more deteriorated compared to the image quality of the region of interest.

The gain control unit 163 controls the gain of the X-ray detector 120 in order to improve the image quality in the region of non-interest, and for describing a gain control method, the structure of the X-ray detector will be first described in detail with reference to FIGS. 12 to 14.

Figure 12:
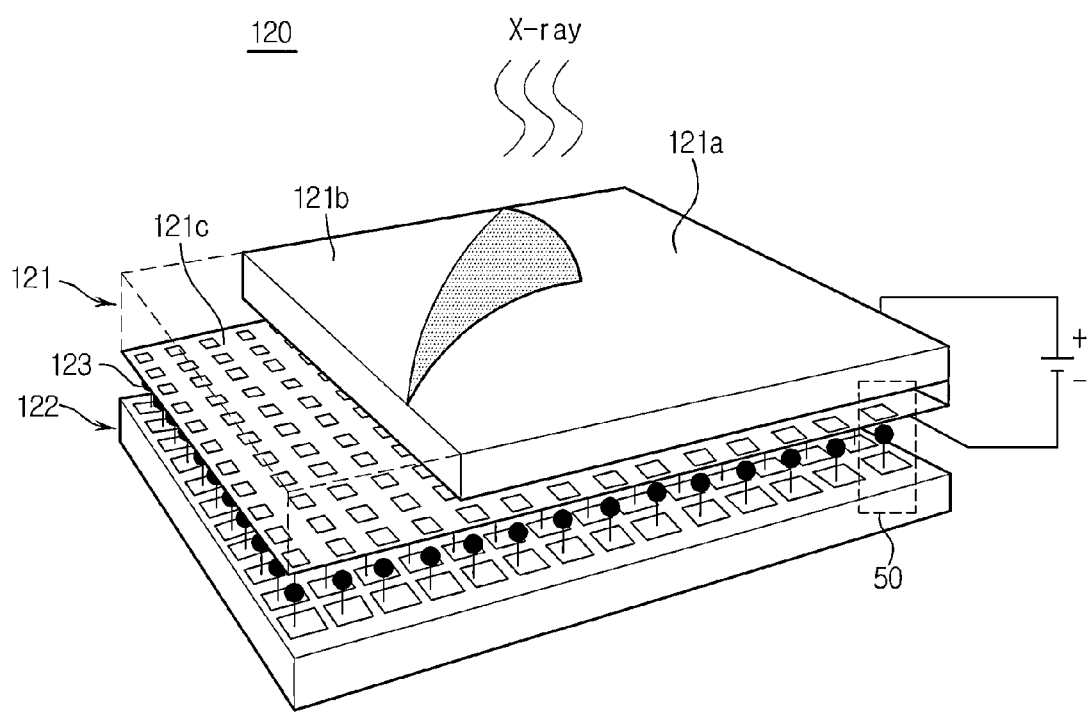
FIG. 12 is a schematic mimetic diagram illustrating a structure of an X-ray detector.

FIG. 12 is a schematic mimetic diagram illustrating a structure of an X-ray detector.

Referring to FIG. 12, the X-ray detector 120 may include a light-receiving element 121 that detects X-rays to generate electrical signals, and a read-out circuit 122 that reads out generated electrical signals.

As the light-receiving element 121, a single crystal semiconductor material may be used in order to ensure a high resolution, a fast response time, and a high dynamic range with low energy and a small dose, and in this instance, Ge, CdTe, CdZnTe, GaAs, or the like may be used as the single crystal semiconductor material.

The light-receiving element 121 may form a PIN photodiode in which a p-type semiconductor substrate 121c with a 2D array structure is joined in a lower portion of a high-resistance n-type semiconductor substrate 121b.

The read-out circuit 122 using a CMOS process may form a 2D array structure to be coupled with the p-type semiconductor substrate 121c of the light-receiving element 121 for each pixel 50. In this instance, as the coupling method, a flip-chip bonding method in which a bump 123 such as solder (PbSn), indium (In), or the like is formed and then is compressed by performing reflow on the bump 123 and applying heat to the bump 123 may be used.

Figure 13:
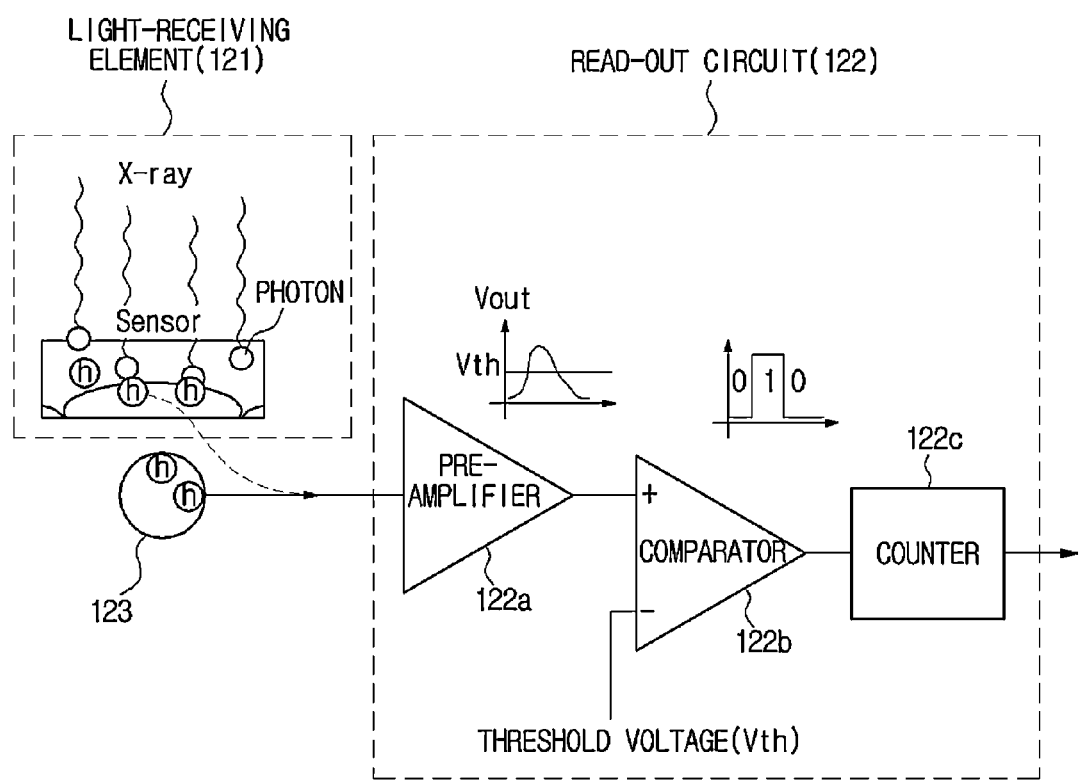
FIG. 13 is a schematic circuit diagram illustrating a single pixel region of the X-ray detector shown in FIG. 12.
Figure 14:
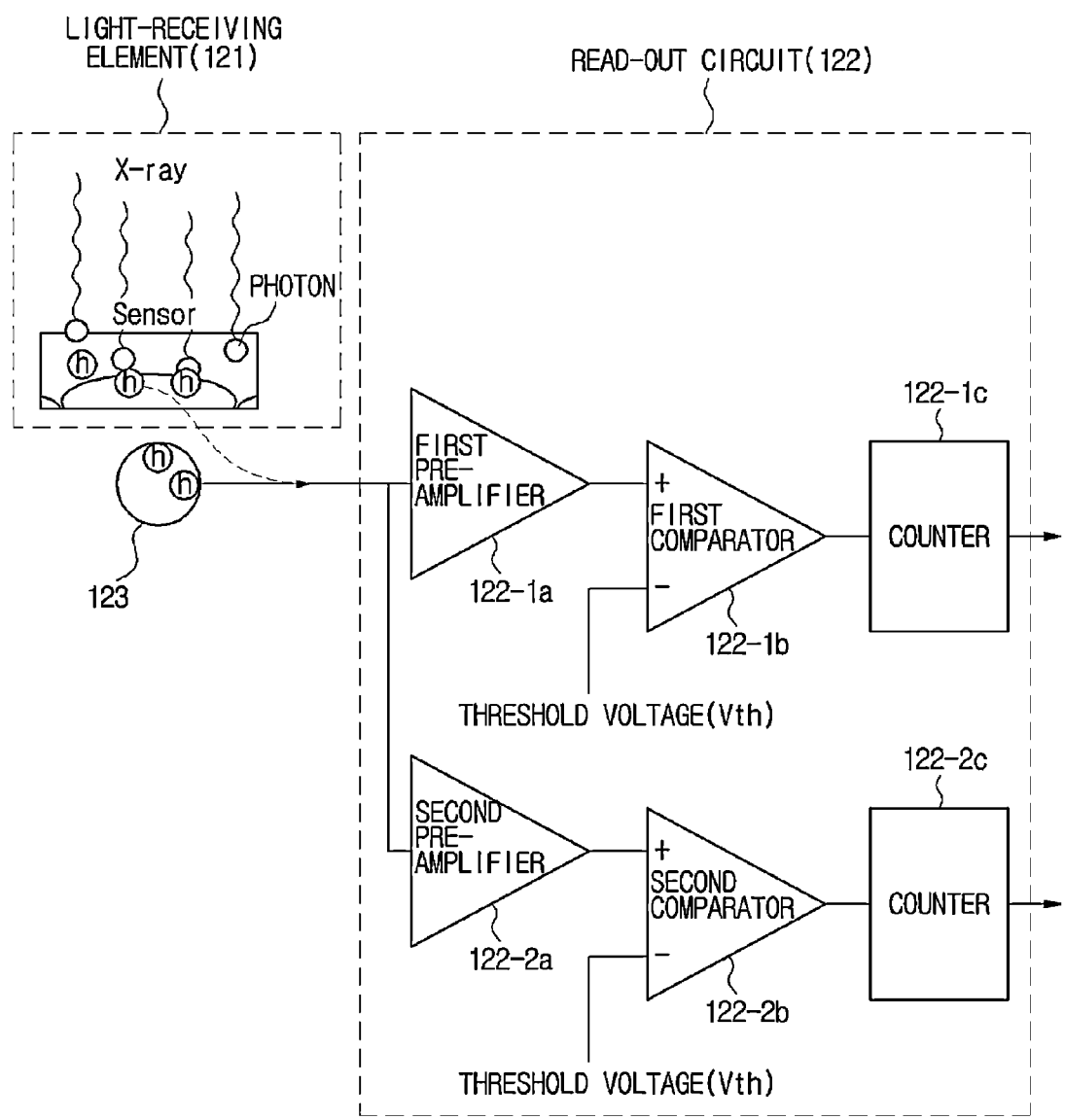
FIG. 14 is a schematic diagram illustrating a single pixel region of an X-ray detector capable of controlling a gain.

FIG. 13 is a schematic circuit diagram illustrating a single pixel region of an X-ray detector shown in FIG. 12, and FIG. 14 is a schematic diagram illustrating a single pixel region of an X-ray detector capable of controlling a gain.

Referring to FIG. 13, when photons of X-rays are made incident on the light-receiving element 121, electrons existing in a valance band receive energy of the photons, and are excited by a conduction band while exceeding a band gap energy difference. Thus, electron-hole pairs may be generated in a depletion region in which there is no electron and hole.

When a metal electrode is formed in each of a p-type layer of the light-receiving element 121 and an n-type substrate and a reverse bias is applied, the electrons among the electron-hole pairs generated in the depletion region are dragged to an n-type region and the holes are dragged to a p-type region. Next, the holes dragged to the p-type region are input to the read-out circuit 122 through bonding of the bump 123.

Charges input to the read-out circuit 122 are transmitted to a pre-amplifier 122a, and voltage signals corresponding to the transmitted charges may be output.

The voltage signals output from the pre-amplifier 122a are transmitted to a comparator 122b, and the comparator compares an arbitrary threshold voltage that can be controlled from the outside and the input voltage signal and outputs a pulse signal of "1" or "0" based on the comparison result. That is, the comparator outputs a signal of "1" when the input voltage is larger than the threshold voltage, and outputs a signal of "0" when the input voltage is smaller than the threshold voltage. A counter may calculate the number of "1" to output data in a digital form.

In this instance, the pre-amplifier 122a is provided as a variable amplifier, and changes a gain by dividing the region of interest and the region of non-interest. Specifically, the pre-amplifier 122a of the pixel 50 corresponding to the region of interest has a first gain, and the pre-amplifier 122a of the pixel 50 corresponding to the region of non-interest has a second gain.

Referring to FIG. 14, each of the pixels 50 of the X-ray detector 120 includes two pre-amplifiers 122-1a and 122-2a having a different gain, and also includes two comparators 122-1b and 122-2b and two counters 122-1c and 122-2c.

A determination as to whether the first pre-amplifier 122-1a or the second pre-amplifier 122-2a is operated is determined in accordance with the particular region which the pixel 50 of the X-ray detector 120 corresponds to. Specifically, when the pixel 50 of the X-ray detector 120 is a pixel of detecting the X-rays transmitted through the region of interest, the charge input to the read-out circuit 122 is transmitted to the first pre-amplifier 122-1*a* to output a voltage signal corresponding to the transmitted charge. On the other hand, when the pixel 50 is a pixel of detecting X-rays transmitted through the region of non-interest, the input charge is transmitted to the second pre-amplifier 122-2*a* to output a voltage signal corresponding to the transmitted charge.

Next, the voltage signal output from the first pre-amplifier 122-1*a* is compared with a threshold voltage of the first comparator 122-1*b* to be counted in the first counter 122-1*c*, and the voltage signal output from the second pre-amplifier 122-2*a* is compared with a threshold voltage of the second comparator 122-2*b* to be counted in the second counter 122-2*c*. In this instance, it is assumed that the threshold voltage of the first comparator 122-1*b* and the threshold voltage of the second comparator 122-2*b* are the same.

When using the X-ray detector 120 having the above-described construction, that is, when each pixel includes a variable amplifier, or when the X-ray detector 120 including a plurality of amplifiers is used, it is possible to control a gain of the X-ray detector 120 in the region of interest and the region of non-interest.

Meanwhile, the above-described structure is merely an example of the X-ray detector 120 capable of controlling a gain, and the X-ray detector 120 may have a variable capacitance element of each pixel of the X-ray detector 120 and have a different capacitance in the region of interest and the region of non-interest. That is, the X-ray detector 120 may be structured in an arbitrary configuration different from those known in the art so long as the X-ray detector 120 can control a gain.

Based on the above-described structure of the X-ray detector 120, a gain control method of the gain control unit 163 will be herein described.

Figure 15:
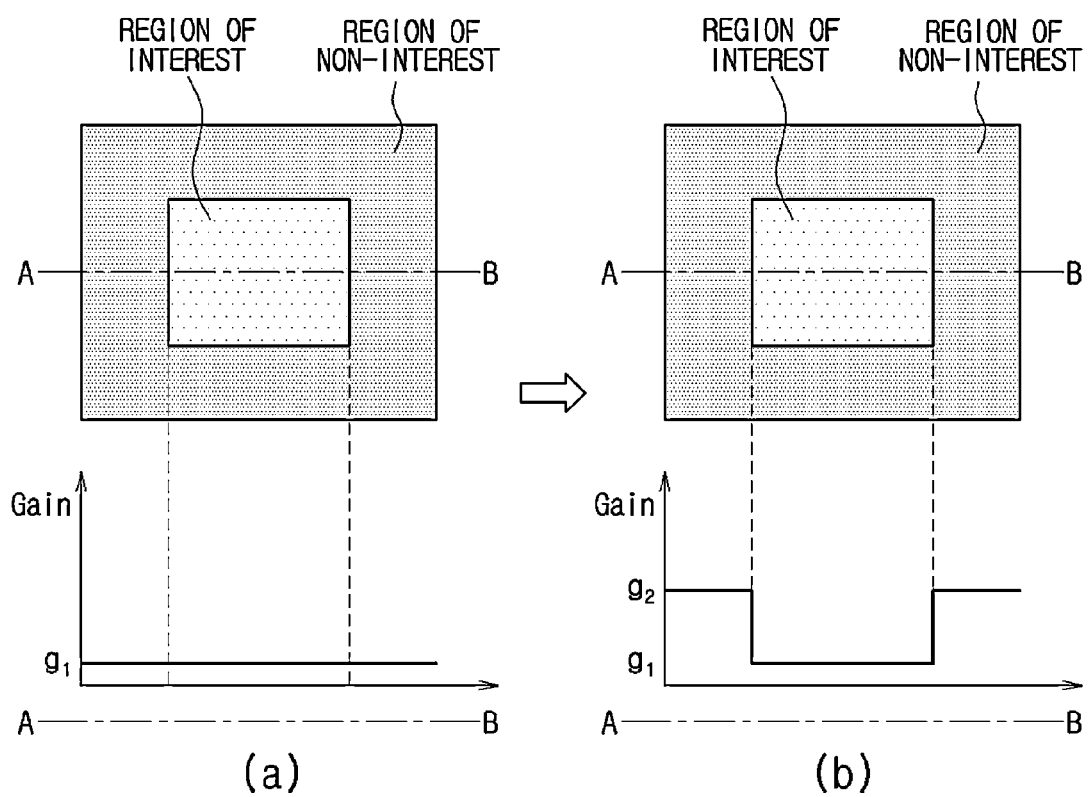
FIG. 15 is a schematic diagram illustrating a gain of an X-ray detector in a region of interest and a region of non-interest.

FIG. 15 is a schematic diagram illustrating a gain of an X-ray detector in a region of interest and a region of non-interest.

In FIG. 15, the region of interest, the region of non-interest, and the straight line AB are the same of those of FIG. 8. Referring again to FIG. 8, the filtering control unit 162 may move the filter 141 for a region of interest to a position corresponding to the region of non-interest among the region of the subject, so that X-rays of a smaller dose than that of X-rays made incident on the region of interest may be made incident on the region of non-interest.

In this instance, the gain control unit 163 may control a gain of the X-ray detector 120 so as to be in inverse proportion to the incident dose of the X-rays. That is, the gain control unit 163 increases, in the region of non-interest where the incident dose of X-rays is relatively small, a gain g1 of the X-ray detector 120 equally applied regardless of the region of interest and the region of non-interest as shown in (a) of FIG. 15. Thus, as shown in (b) of FIG. 15, the gain of the X-ray detector 120 becomes higher in the region of non-interest rather than in the region of interest (g1<g2).

When applying this feature to the X-ray detector 120 including the plurality of amplifiers of FIG. 14, a gain of the second pre-amplifier 122-2*a* may be higher than a gain of the first pre-amplifier 122-1*a*. When it is assumed that the same charge is input, a voltage signal output from the second pre-amplifier 122-2*a* becomes greater than a voltage signal output from the first pre-amplifier 122-1*a*, and the former rather than the latter is highly likely to exceed the threshold voltage. Thus, a counting probability of the second counter 122-2*c* becomes larger than that of the first counter 122-1*c*, which leads to a result that the gain of the X-ray detector 120 in the region of non-interest becomes higher than that in the region of interest. That is, in the structure of the X-ray detector 120 shown in FIG. 14, the gain control unit 163 determines the gain of the pre-amplifiers 122-1*a* and 122-2*a*, and therefore it is possible to indirectly control the gain of the X-ray detector 120.

Similarly, in the X-ray detector 120 including the variable amplifier of FIG. 13, the gain control unit 163 may enable a second gain of the pre-amplifier 122*a* of the pixel 50 corresponding to the region of non-interest to be higher than a first gain of the pre-amplifier 122*a* of the pixel 50 corresponding to the region of interest, and therefore the gain of the X-ray detector 120 may be increased in the region of non-interest.

In addition, this may be applied to even the structure in which each pixel of the X-ray detector 120 includes the variable capacitance element. When the element of the pixel corresponding to the region of interest has a larger capacitance than that of the element of the pixel corresponding to the region of non-interest, the gain of the X-ray detector 120 in the region of non-interest becomes higher than that in the region of interest. Thus, the gain control unit 163 indirectly controls the gain of the X-ray detector 120 by adjusting the capacitance of the variable capacitance element as described above.

Meanwhile, when the gain of the X-ray detector 120 is increased in the region of non-interest as described above, the SNR in the region of non-interest is also increased. That is, the image quality of the region of non-interest may be improved, and a difference in the image qualities of the region of interest and the region of non-interest may be reduced.

Figure 16:
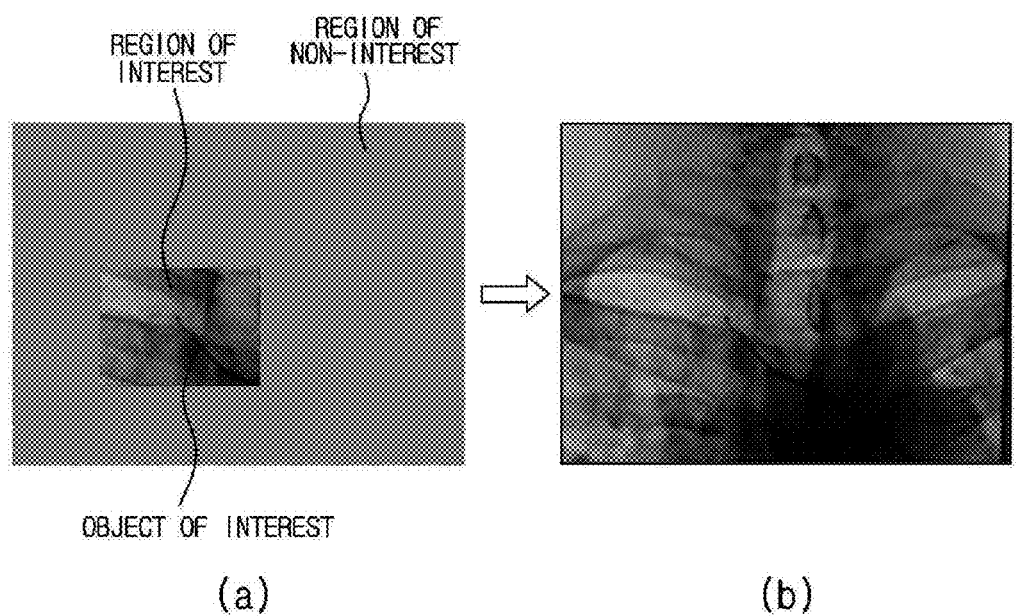
FIG. 16 is a diagram illustrating improvement in image quality of a region of non-interest according to gain adjustment.

FIG. 16 is a diagram illustrating improvement in image quality of a region of non-interest according to gain adjustment.

Specifically, in FIG. 16, a case in which a predetermined region including an instrument that is an object of interest is set as the region of interest and frame images obtained in such a manner that X-rays of a smaller dose than that of X-rays made incident on the region of interest are made incident on the region of non-interest is shown. In (a) of FIG. 16, a frame image obtained by equally applying a gain of the X-ray detector 120 regardless of the region of interest and the region of non-interest is shown, and in (b) of FIG. 16, a frame image obtained by increasing the gain of the X-ray detector 120 applied to (a) of FIG. 16 only in the region of non-interest is shown.

The region of non-interest shown in (a) of FIG. 16 has a low SNR, and therefore noise is generated to cause poor image quality. However, the region of non-interest shown in (b) of FIG. 16 has a high SNR, and therefore a difference in the image qualities between the region of interest and the region of non-interest hardly appears.

Meanwhile, controlling the gain of the X-ray detector 120 by the gain control unit 163 relies on the filtering control unit 162. For example, when the filtering control unit 162 controls a thickness of the filter 141 for a region of interest so that a difference of doses of X-rays made incident on the region of interest and the region of non-interest is increased, a difference in the image qualities of the two regions may be increased in proportion to the increase in the difference of doses of X-rays. The gain control unit 163 is provided in order to maximally reduce the difference of the image qualities, and therefore the gain control unit 163 controls a difference in the gains of the X-ray detector 120 to be increased.

As above, the configuration of the X-ray imaging apparatus and the operations of the configuration thereof have been described based on the exemplary embodiments, and a control method for the X-ray imaging apparatus will be described with reference to the exemplified flowchart.

FIG. 17 is a flowchart illustrating a control method for an X-ray imaging apparatus in accordance with an exemplary embodiment. In the control method for the X-ray imaging apparatus, the X-ray imaging apparatus 100 may be used.

Referring to FIG. 17, in operation 310, X-rays are radiated to a region of a subject at a predetermined time interval. The X-rays may be continuously radiated, but here, a pulse exposure method in which X-rays are radiated at a predetermined time interval in order to reduce a dose of X-rays and improve temporal resolution is adopted. Here, the predetermined time interval may be determined according to a pulse rate, and as an example, when the pulse rate is 30 pulses per second (30 pps), X-rays are radiated 30 times per second.

In operation 320, a frame image about the region of the subject is acquired by detecting the radiated X-rays. Here, the region of the subject may coincide with an X-ray radiography region, and acquisition of the frame image may be synchronized with the radiation of X-rays to be performed in real time.

In operation 330, information about the region of interest is acquired from the frame image about the region of the subject. Specifically, an object of interest is detected from the frame image about the region of the subject, and a predetermined region including the detected object of interest is set as the region of interest. The position and size of the region of interest may be determined considering the position and size of the object of interest or movement characteristics of the object of interest, and uncertainty of the movement characteristics of the object of interest may be also considered. The information about the region of interest may include the position and size of the region of interest or movement characteristics thereof, and the movement characteristics of the region of interest may be defined by the movement characteristics of the object of interest.

In this instance, in operation 340, whether the object of interest or the region of interest is present is determined. When the information about the region of interest cannot be acquired due to absence of the object of interest or the region of interest, an X-ray diagnosis process is terminated.

When the region of interest is present so that the information about the region of interest is acquired, operation 350 is performed. That is, in operation 350, the filtering unit 140 is controlled in such a manner that X-rays of a smaller dose than that of X-rays made incident on the region of interest are made incident on the region of non-interest, and the X-ray detector 120 is controlled in such a manner that a gain of the X-ray detector 120 in the region of non-interest is larger than that in the region of interest.

The filtering unit 140 may include the filter 141 for a region of interest which is made of a material for attenuating X-rays, and the position of the filter 141 for a region of interest may be controlled between the X-ray source 110 that radiates X-rays and the X-ray detector 120 that detects X-rays. Thus, when the filter 141 for a region of interest is positioned in a position corresponding to the region of non-interest, X-rays of a smaller dose than that of X-rays made incident on the region of interest may be made incident on the region of non-interest. Setting of the region of interest may be performed in real time according to a frame rate, and when the region of interest is moved, the filter 141 for a region of interest may be moved to the position corresponding to the region of non-interest by tracking the movement of the region of interest.

Meanwhile, control of the filter 141 for a region of interest may include adjusting a difference in doses of X-rays to be made incident on the region of interest and the region of non-interest based on information about image characteristics such as noise, motion, contrast, and the like.

Since X-rays of a small dose are made incident on the region of non-interest, a low SNR appears in the region of non-interest of the frame image, which leads to deterioration of the image quality in the region of non-interest. Thus, in order to improve the image quality in the region of non-interest, the gain of the X-ray detector 120 may be controlled to be more increased in the region of non-interest compared to the region of interest.

In this instance, a difference in the gains in the region of interest and the region of non-interest may be controlled to be in proportion to the difference in the doses of X-rays made incident on the two regions.

In operation 360, when increasing the gain of the X-ray detector in the region of non-interest while having the difference in the doses of X-rays made incident on the region of interest and the region of non-interest, the frame image in which the dose of the X-rays made incident on the subject is reduced and the image quality of the region of non-interest is improved may be acquired.

In this instance, correction and enhancement for improving the image quality of the image may be performed in the entire region of the frame image. That is, the frame image may be corrected using a spatial filter, a temporal filter, a spatio-temporal filter, and a denoising algorithm such as super-resolution reconstruction. In addition, the frame image may be enhanced using a detail enhancement algorithm such as a contrast enhancement algorithm based on histogram or wavelet, an edge enhancement filter, and the like.

In operation 370, the acquired frame image is displayed on the display unit in real time.

As described above, according to the X-ray imaging apparatus and the control method for the same, the region of interest and the region of non-interest may be separated and the gain of the X-ray detector as well as an incident dose of X-rays may differ for each region, thereby generating a high quality image using a low dose. In addition, movement of the region of interest may be possible, and therefore the X-ray imaging apparatus and the control method for the same may be applied to the field of X-ray video.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray imaging apparatus comprising:
    an X-ray source configured to radiate X-rays to a region of a subject;
    an X-ray detector configured to acquire a plurality of frame images related to the region of the subject by detecting the radiated X-rays;
    a filter configured to filter the X-rays radiated from the X-ray source;
    an image processor configured to set a region of interest within the region of the subject based on the plurality of frame images; and a controller configured to control the filter so that X-rays of a lower dose than a dose of X-rays made incident on the region of interest are made incident on a region of non-interest within the region of the subject, and control the X-ray detector so that a gain of the X-ray detector in the region of non-interest is greater than a gain of the X-ray detector in the region of interest.

2. The X-ray imaging apparatus according to claim 1, wherein the controller is configured to control the X-ray detector in such a manner that a gain difference between the gain of the X-ray detector in the region of non-interest and the gain of the X-ray detector in the region of interest is proportional to a difference between the dose of the X-rays made incident on the region of non-interest and the dose of the X-ray made incident on the region of interest.

3. The X-ray imaging apparatus according to claim 1, wherein the filter comprises:
   a filter for the region of interest that is made of a filter material for attenuating the X-rays, and
   a filter driver configured to move the filter for the region of interest.

4. The X-ray imaging apparatus according to claim 3, wherein the image processor is configured to acquire information about the region of interest and information about image characteristics based on the plurality of frame images, and transmit the acquired information to the controller.

5. The X-ray imaging apparatus according to claim 4, wherein the information about the region of interest is at least one of a position of the region of interest, a size of the region of interest, and a movement characteristic of the region of interest.

6. The X-ray imaging apparatus according to claim 4, wherein the controller is configured to control the filter driver in such a manner that the filter driver moves the filter for the region of interest to a position corresponding to the region of non-interest based on the information about the region of interest.

7. The X-ray imaging apparatus according to claim 4, wherein the controller is configured to determine a difference in the doses of the X-rays made incident on the region of non-interest and the region of interest based on the information about image characteristics.

8. The X-ray imaging apparatus according to claim 7, wherein the controller is configured to control a kind or a thickness of the filter for the region of interest according to the determined difference in the doses of the X-rays.

9. The X-ray imaging apparatus according to claim 1, wherein each pixel of the X-ray detector comprises a variable amplifier or a plurality of amplifiers.

10. The X-ray imaging apparatus according to claim 9, wherein the controller is configured to control the X-ray detector in such a manner that the amplifier of a pixel corresponding to the region of interest has a first gain, the amplifier of a pixel corresponding to the region of non-interest has a second gain, and the first gain is smaller than the second gain.

11. The X-ray imaging apparatus according to claim 1, wherein each pixel of the X-ray detector comprises a variable capacitance element.

12. The X-ray imaging apparatus according to claim 11, wherein the controller is configured to control the X-ray detector in such a manner that the variable capacitance element of a pixel corresponding to the region of interest has a first capacitance, the variable capacitance element of a pixel corresponding to the region of non-interest has a second capacitance, and the first capacitance is greater than the second capacitance.

13. The X-ray imaging apparatus according to claim 1, wherein the image processor is configured to perform setting of the region of interest in real time according to a frame rate.

14. A control method for an X-ray imaging apparatus, the control method comprising:
   radiating, by an X-ray source, X-rays to a region of a subject;
   acquiring, by an X-ray detector, a plurality of frame images related to the region of the subject by detecting the radiated X-rays;
   setting a region of interest within the region of the subject based on the plurality of frame images;
   filtering the X-rays radiated from the X-ray source so that X-rays of a lower dose than a dose of X-rays made incident on the region of interest are made incident on a region of non-interest within the subject; and
   controlling the X-ray imaging apparatus in such a manner that a gain of the X-ray detector in the region of non-interest is greater than a gain in the region of interest.

15. The control method for the X-ray imaging apparatus according to claim 14, wherein the controlling comprises controlling the X-ray imaging apparatus in such a manner that a gain difference of the X-ray detector in the region of non-interest and the region of interest is proportional to a difference in the doses of the X-rays made incident on the region of non-interest and the region of interest.

16. The control method for the X-ray imaging apparatus according to claim 14, further comprising acquiring information about the region of interest and information about image characteristics based on the plurality of frame images.

17. The control method for the X-ray imaging apparatus according to claim 16, wherein the filtering of the X-rays comprises moving a filter for the region of interest that attenuates the radiated X-rays to a position corresponding to the region of non-interest based on the information about the region of interest.

18. The control method for the X-ray imaging apparatus according to claim 16, wherein the filtering of the X-rays comprises determining a difference in the doses of the X-rays made incident on the region of non-interest and the region of interest based on the information about image characteristics, and controlling a kind or a thickness of the filter for the region of interest according to the determined difference in the doses of the X-rays.

19. The control method for the X-ray imaging apparatus according to claim 14, wherein the controlling comprises controlling the X-ray imaging apparatus in such a manner that each pixel of the X-ray detector comprises a variable amplifier or a plurality of amplifiers, the amplifier of a pixel corresponding to the region of interest has a first gain, the amplifier of a pixel corresponding to the region of non-interest has a second gain, and the first gain is smaller than the second gain.

20. The control method for the X-ray imaging apparatus according to claim 14, wherein the controlling comprises controlling the X-ray imaging apparatus in such a manner that, when each pixel of the X-ray detector includes a variable capacitance element, the variable capacitance element of a pixel corresponding to the region of interest has a first capacitance, and the variable capacitance element of a pixel corresponding to the region of non-interest has a second capacitance, setting the first capacitance to be greater than the second capacitance.

* * * * *